(12) United States Patent
Bohlman et al.

(10) Patent No.: US 10,675,126 B2
(45) Date of Patent: Jun. 9, 2020

(54) COMBINATION LIP RETRACTOR AND GUARD WITH INTEGRATED LIGHT SOURCE, SUCTION, AND SURGICAL SMOKE PLUME FILTER

(71) Applicants: Chris Bohlman, Annapolis, MD (US); Michael Cunningham, Edgewater, MD (US)

(72) Inventors: Chris Bohlman, Annapolis, MD (US); Michael Cunningham, Edgewater, MD (US)

(*) Notice: Subject to any disclaimer, the term of this patent is extended or adjusted under 35 U.S.C. 154(b) by 642 days.

(21) Appl. No.: 14/971,034

(22) Filed: Dec. 16, 2015

(65) Prior Publication Data

US 2016/0175067 A1 Jun. 23, 2016

Related U.S. Application Data

(60) Provisional application No. 62/093,233, filed on Dec. 17, 2014, provisional application No. 62/151,574, filed on Apr. 23, 2015.

(51) Int. Cl.
*A61C 5/90* (2017.01)
*A61B 18/00* (2006.01)

(52) U.S. Cl.
CPC ...... *A61C 5/90* (2017.02); *A61B 2018/00327* (2013.01); *A61B 2218/008* (2013.01)

(58) Field of Classification Search
CPC .......... A61C 5/90; A61B 1/06; A61B 1/0607; A61B 1/0615
USPC .................. 600/208, 235, 237, 248; 128/849
See application file for complete search history.

(56) References Cited

U.S. PATENT DOCUMENTS

| | | | | |
|---|---|---|---|---|
| 2,280,992 A | * | 4/1942 | Wright | A61M 1/0031 600/573 |
| 3,916,880 A | * | 11/1975 | Schroer | A61B 1/24 600/205 |
| 6,957,907 B2 | * | 10/2005 | Fischer | A61B 5/0088 362/16 |
| 6,964,570 B2 | * | 11/2005 | Ghim | A61C 5/90 433/140 |
| 2008/0113312 A1 | * | 5/2008 | Ortega | A61C 5/90 433/29 |

* cited by examiner

*Primary Examiner* — Anu Ramana
(74) *Attorney, Agent, or Firm* — Duane Morris LLP

(57) ABSTRACT

A surgical guard configured to protect a patient's oral cavity during surgery is disclosed. The surgical guard includes a first arcuate wing comprising a first end and a second end and a second arcuate wing comprising a first end and a second end. A wing connector couples the first end of the first arcuate wing and the first end of the second arcuate wing. The first arcuate wing, the second arcuate wing, and the wing connector are configured to retract and insulate the lips and oral commissure of a patient during oral surgery.

19 Claims, 23 Drawing Sheets

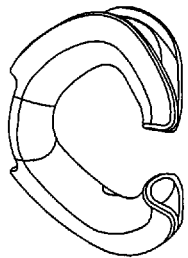
FIG. 20G
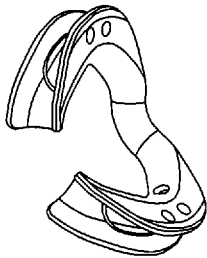
FIG. 20H
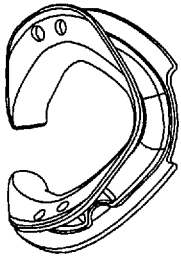
FIG. 20I
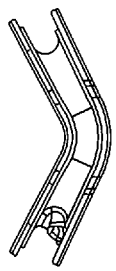
FIG. 20A
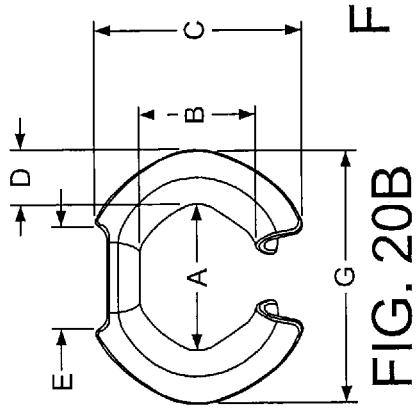
FIG. 20C
FIG. 20B
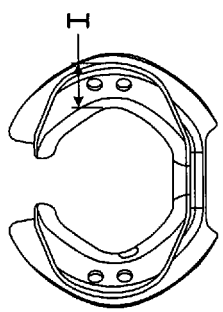
FIG. 20E
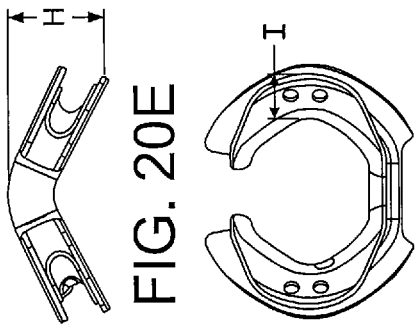
FIG. 20F
FIG. 20D

COMBINATION LIP RETRACTOR AND GUARD WITH INTEGRATED LIGHT SOURCE, SUCTION, AND SURGICAL SMOKE PLUME FILTER

CROSS-REFERENCE TO RELATED APPLICATIONS

This application claims benefit under 35 U.S.C. § 119(e) to U.S. Provisional Appl. No. 62/093,233, filed Dec. 17, 2014, entitled "COMBINATION LIP RETRACTOR AND GUARD WITH INTEGRATED SUCTION" and U.S. Provisional Appl. No. 62/151,574, filed Apr. 23, 2015, entitled "COMBINATION LIP RETRACTOR AND GUARD WITH INTEGRATED LIGHT SOURCE, SUCTION, AND SURGICAL SMOKE PLUME FILTER," the disclosure of each of which is incorporated herein in its entirety.

BACKGROUND

Some of the more common adverse events that occur during ENT and oral surgery resulting from the use of electrosurgical units (ESUs) and powered or manual instrumentation include: (1) inadvertent burns to the lips and specifically the oral commissure; (2) inadvertent damage to the lips with powered or manual instrumentation; (3) airway fire; and (4) potentially hazardous smoke plume in the surgical environment.

Lip burns may be caused in several ways. For example the surgeon may touch an activated electrosurgical device to a metal instrument (such as an Allis clamp, forceps, or Hurd retractor) that is resting upon the oral commissure, thus sending energy up the instrument to the lip at the point of contact. Lip burns may also happen when the surgeon fails to deactivate the electrosurgical device as it is removed from the mouth, resulting in the electrode inadvertently contacting the patient's lip upon exit. Also, any malfunction that would cause insulation on the shaft of the electrosurgical device to melt around the area of the lips may cause lip burns. Damage to the lips may also occur during inadvertent contact with powered instrumentation such as drills and burs during oral and trans oral surgery. A number of methods may be employed to mitigate damage to the lips including insertion of dental cheek and lip retractors commonly for teeth whitening, draping of wet gauze over the lips and oral commissure, and use of the surgeon's gloved fingers as an insulator between ESUs, metal instruments, and the patient's lips. However, each of these methods presents one or more drawbacks, as discussed below.

Airway fires may occur when there is an ignition source, an oxidizer, and fuel present. Electrosurgical units (ESUs) may provide the ignition source, and during otolaryngology (ENT) surgeries, such as a tonsillectomy, the oral cavity may allow the collection of gases and an oxygen-enriched atmosphere (OEA). This gas or smoke may also collect as many ENT surgeons chose to operate with a paddle or needle tip electrocautery device that does not have integrated suction to remove accumulating gases and smoke. An additional surgical staff member may often hold a suction tip at the edge of the mouth to evacuate smoke and leaking gases. However, if this assistant loses attention or improperly holds the suction, gases may collect in the oral cavity, increasing fire risk. Likewise, if the patient is suspended via a mayo stand, the surgical staff member responsible for suction gas and smoke has been found to have a tendency to grow tired during the procedure and lean on the mayo stand, thus increasing the risk of dislocating the patient's jaws. Fine-dissecting electrosurgical tips with integrated suction are now available, yet they are rarely used as surgeons prefer the unencumbered feel of a device without suction tubing attached.

Studies have also shown that smoke plume resulting from electrosurgical devices may be a carcinogen, a mutagen, and an infectious vector capable of causing harm to the surgical staff. Literature suggests that surgical smoke is comprised of over 150 chemicals, including benzene, hydrogen cyanide, toluene, perchloroethylene, formaldehyde, acrylonitrile, and ethylbenzene. One study suggests that one day of surgical smoke exposure in an operating theatre is equal to the carcinogen effects of 27 cigarettes. HPV, HIV, and hepatitis pathogens capable of transmitting disease have also been found in surgical smoke plume. Again, the surgical assistant holding a suction device is the most widely used solution to remove these potentially hazardous electrosurgical by-products, with similar potential disadvantages to those discussed above. Gas and surgical smoke plume evacuation may be particularly challenging during TransOral Robotic Surgery (TORS).

Oral retractors in use today, such as the dental lip and cheek retractors commonly used for teeth whitening procedures, do not provide the unique requirements for an ENT or oral surgeon, as they are predominantly designed for visual access to the teeth only in a closed-jaw position. ENT, oral and maxillofacial surgeons more often require easy access to the oral cavity, nasopharynx, oropharynx, and laryngopharynx; adequate burn and damage protection of the lips and oral commissure from either electrosurgical devices or powered instrumentation; design allowance for the mouth gag/retractor (i.e., Crowe-Davis, McIvor, Whitehead, Molt, Denhart, Roser-Koenig, Fergusson-Ackland, Jennings, Kilner-Doughty, Davis-Boyle, Dingmann, FK-WO TORS, etc.) and airway tube; design allowance for elongated geometry of oral cavity during mouth gag suspension; construction from a non-flammable, heat-resistant material; and a need to keep the surgical site clear of obstructions such as suction tubing, etc., that may inhibit a surgeon's view or movement, and a need to evacuate smoke/gas.

Headlights utilized for standard illumination of the oral cavity are expensive, cumbersome, and can present hazards in the operating suite due to the tethering of the light source to the surgeon and potential fire risks. In academic teaching institutions, resident and attending surgeons often share one head light during surgery, compromising the sterile field. In emergency situations, such as a post-operative tonsillectomy hemorrhage, peritonsillar abscess, or foreign body admitted to an Emergency Department, proper illumination can be difficult to achieve, resulting in compromised patient safety. Overseas and low income medical work is often hindered by lack of access to proper lighting as well, impacting the level of care traveling oropharyngeal surgeons can provide to patients.

Visual access to the oral cavity is limited, especially in teaching situations where a surgical resident, medical student, attending surgeon, or other observer must look over the shoulder of the operating surgeon to visualize the procedure as it unfolds. Various retractors have been utilized to spread the lips and cheeks laterally to improve visual access with limited success.

Postoperative hemorrhage is one of the primary concerns of tonsil surgeons, and has been for over 3,000 years. Numerous methods have been devised to locate and seal blood vessels intraoperatively. However, no single technique has stood out in solving the problem of postoperative hemorrhage and identification of blood vessels at or near the surface of the surgical area is problematic. Post-op bleeds requiring surgical intervention still occur after 5 percent of all tonsillectomies.

SUMMARY

In various embodiments, a surgical guard configured to protect a patient's oral cavity during surgery is disclosed. The surgical guard includes a first arcuate wing comprising a first end and a second end and a second arcuate wing comprising a first end and a second end. A wing connector couples the first end of the first arcuate wing and the first end of the second arcuate wing. The first arcuate wing, the second arcuate wing, and the wing connector are configured to retract and insulate the lips and oral commissure of a patient during oral surgery.

In various embodiments, a method of retracting and guarding the oral commissure is disclosed. The method includes the step of reducing a horizontal dimension of a lip retractor and guard such that the lip retractor and guard fit within an oral cavity proximal to oral commissures. The lip retractor and guard comprises a first arcuate wing comprising a first end and a second end, a second arcuate wing comprising a first end and a second end, and a wing connector coupling the first end of the first arcuate wing and the first end of the second arcuate wing. A first oral commissure is nested within the first arcuate wing and a second oral commissure is nested within the second arcuate wing. The lip retractor is released such that the horizontal dimension of the lip retractor increases and retracts the oral cavity away from a predefined surgical field.

In various embodiments, a lip retractor and guard is disclosed. The lip retractor and guard comprises a first arcuate shaped wing and a second arcuate shaped wing. Each of the first arcuate shaped wing and the second arcuate shaped wing include a first end and a second end. A wing connector is coupled between the first end of the first arcuate shaped wing and the first end of the second arcuate shaped wing. At least one of the first arcuate shaped wing, the second arcuate shaped wing, or the wing connector are deformable to compress the first arcuate shaped wing and the second arcuate shaped wing. At least one light-emitting diode (LED) is formed integrally with an inner side of at least one of the first arcuate shaped wing, the second arcuate shaped wing, and the wing connector. The at least one LED is configured to illuminate a body cavity.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIGS. 20A-20I show various views of a combination lip retractor and guard, in accordance with various embodiments;

DETAILED DESCRIPTION

Figure 1:
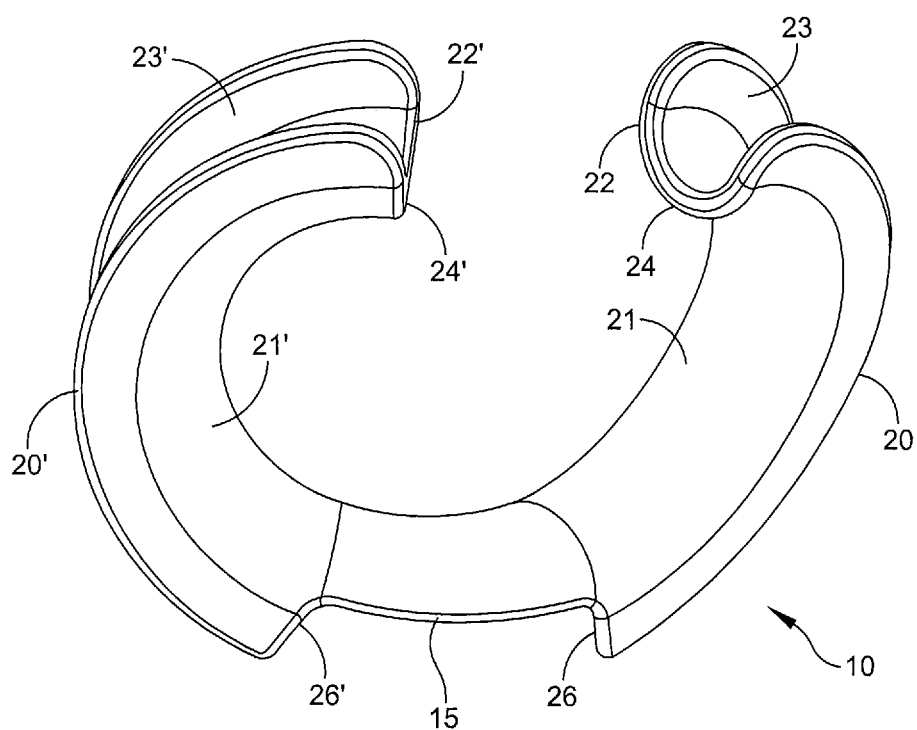
FIG. 1 shows a perspective view of the lip retractor, in accordance with various embodiments.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to" Also, the term "couple" or "couples" is intended to mean either an indirect or direct connection. Thus, if a first device couples to a second device, that connection may be through a direct connection, or through an indirect connection via other devices, components, and connections. Further, the terms "proximal" and distal are intended to refer to proximity relative to a clinician. Thus, if a first device is distal and a second device is proximal, the second device is nearer to the clinician than the first device.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this disclosure belongs.

Where a range of values is provided, it is understood that every intervening value, between the upper and lower limit of that range and any other stated or intervening value in that stated range is encompassed within the disclosure. Also, it is contemplated that any optional feature of the inventive variations described may be set forth and claimed independently, or in combination with any one or more of the features described herein.

Before the various embodiments are described in detail, it is to be understood that this disclosure is not limited to particular variations set forth herein as various changes or modifications may be made, and equivalents may be substituted, without departing from the spirit and scope of the disclosure. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. In addition, many modifications may be made to adapt a particular situation, material, composition of matter, process, process act(s) or step(s) to the objective(s), spirit or scope of the present disclosure. All such modifications are intended to be within the scope of the claims made herein.

FIG. 1 shows a perspective view of a combination lip retractor and guard 10 embodiment according to the current disclosure, preferably for use in oropharyngeal surgery. This figure shows the general form of the lip retractor 10, and is preferably constructed as a one piece design, formed from a semi-flexible, heat resistant, nonflammable material, such as, for example silicon. Generally, the retractor includes two wing portions 20 and 20' approximately opposite each other and a mirror image of each other, and a wing connector 15 therebetween, all of which are cooperatively operable to retract a patient's lips and keep the pathway for the surgeon clear. Each wing 20 and 20' is an elongate arcuate or approximate "C" shape and has a channel cross section 22 and 22'. The channel may be shaped and sized so as to easily and atraumatically nest and protect the patient's lips and oral commissure. The wings 20 and 20' may be placed adjacent the oral commissure and in order to provide a barrier operable to protect the lips from heat and electrical current, as well as any sharp objects in the field. The wing channel or troughed cross section 22 and 22' includes a curved base portion 21 and 21' as well as lateral walls 23 and 23' that extend approximately laterally from curved base portion 21 and 21'. The wing curved portions 21 and 21' atraumatically nest and retract the patient's mouth while the lateral walls 23 and 23' are operable to provide adequate or additional coverage of the oral commissure and protect the lips from inadvertent damage.

As shown in this embodiment, the wing cross sections 22 and 22' are approximately constant in dimensions along the length or curvature of the wing. In alternative embodiments the cross sectional wall thicknesses may vary in both or either of the curved portions 21 and 21' and the lateral walls 23 and 23' to provide a more ergonomic wing shape or better protection from adverse events. Lateral walls 2S and 2S' may also vary in length along the length or curvature of the wings 20 and 20', for similar reasons. Wings 20 and 20' are elongate and ergonomically curved so that they may match a patient's natural open mouth curvature, with one free end 24 and 24' and one connected end 26 and 26'. Lip retractor 10 also includes a flexible wing connector 15 that provides a bridge between the two wings 20 and 20' and is connected at the wing connected ends 26 and 26'. Wing connector 15 provides structural support to the retractor 10.

Figure 2:
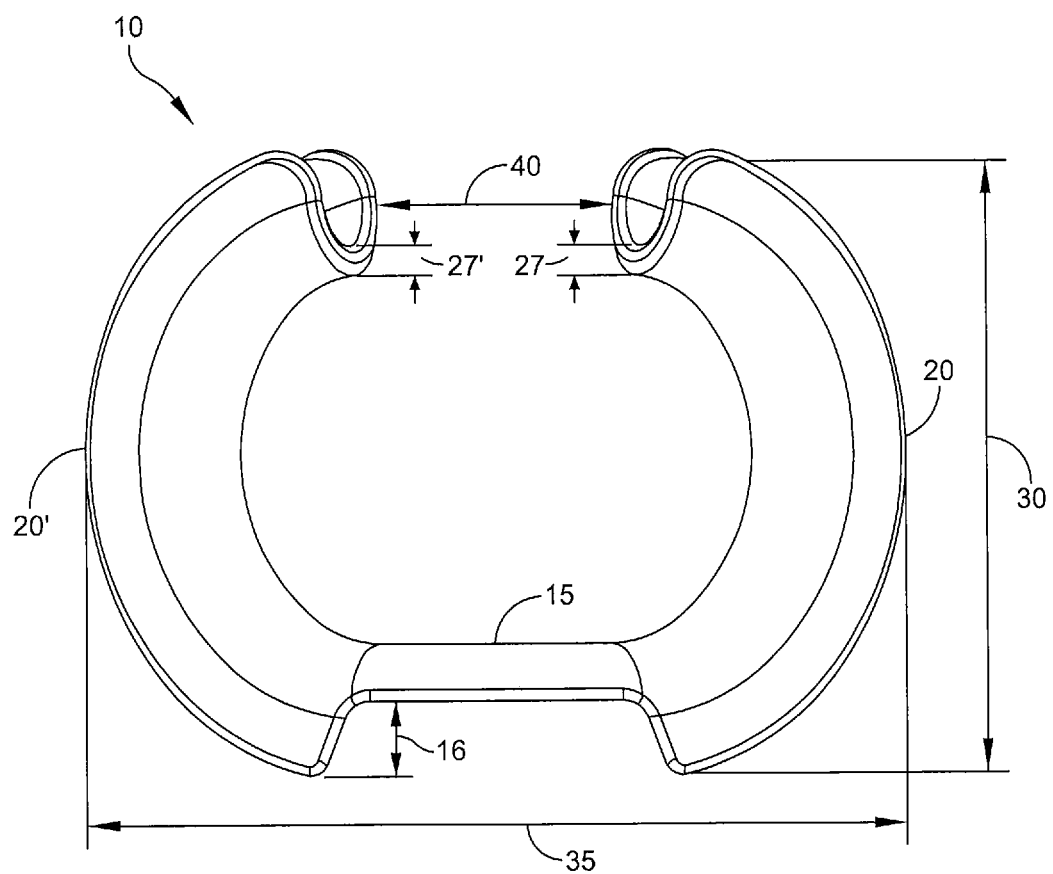
FIG. 2 shows a top down view of the lip retractor and guard showing the wing connector thickness, in accordance with various embodiments.
Figure 5:
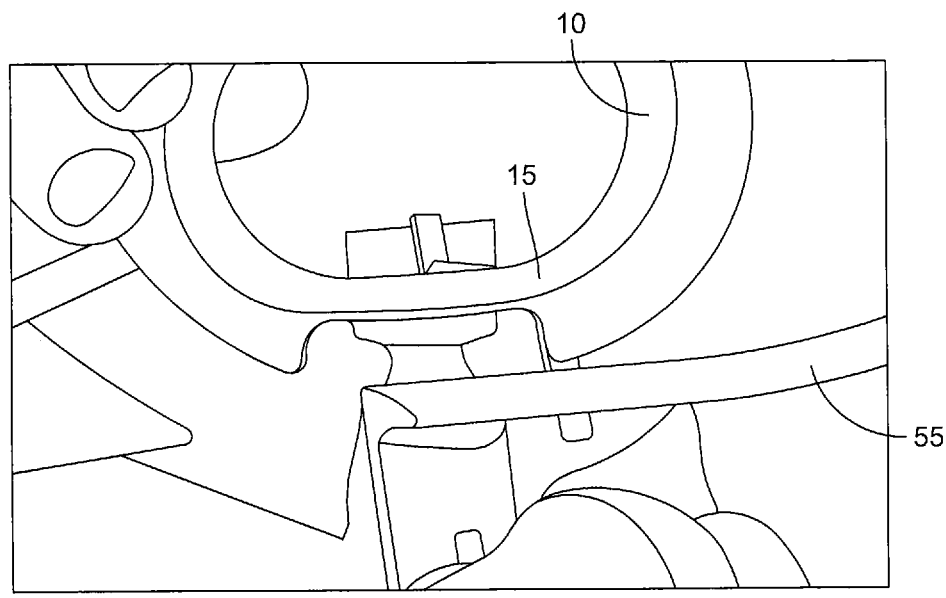
FIG. 5 shows a tongue blade accommodated beneath the lip retractor wing connector, in accordance with various embodiments.

In FIG. 2, the thickness of the wing connector 15 may be seen from this top down view. In operation, the wing connector 15 may be placed near the patient's lower lip and may be notched so as to leave a gap 16 to space the wing connector slightly from the patient's lower lip, to allow for instrumentation to have access into the mouth and throat by sliding an instrument between the patient's lower lip and inferior side of connector 15 with minimal obstruction to the surgical field. Alternatively, the instrumentation may be placed first and the retractor 10 may easily fit over instrumentation, more specifically the wing connector 15 inferior side may easily slide over instrumentation during placement of retractor 10 on lips. Instruments may include a tongue blade and ET tube, and are shown in FIG. 5. Wing connector 15 may be solid so as to provide structural support to the retractor 10 and preferably has sufficient stiffness so as to provide the retraction force for the retractor 10. Overall the retractor vertical dimension 30 and horizontal dimension 35 may be preferentially sized so as to ergonomically fit with the patient's mouth size. Dimensions 30 and 35 may be approximately 2.4 inches and 3.3 inches respectively, but may be produced in a variety of sizes to accommodate young children and adults. It is contemplated that a variety of sizes of retractor 10 may be suitable and desirable for practical use.

Wing free ends 24 and 24' terminate so as to leave a superior horizontal gap 40 that is generally sized so as to allow for instrumentation (shown in FIG. 6) access to the oral cavity while minimizing obstruction to the surgical field. Instrumentation may include teeth retractors and wing free ends 24 and 24' may be sized and shaped so as to work cooperatively with typical surgical instrumentation such as teeth retractors. Wings 20 and 20' are generally a constant cross sectional thickness 27 and 27', although this thickness 27 and 27' may vary as described earlier. Thickness 27 and 27' is preferably sufficient to provide adequate resistance to heat and electrical current from surgical instrumentation, given the material choice of manufacture. It has been determined that a thickness of approximately 0.1 cm may be sufficient, to provide the protection required, if the material is a flexible polyurethane or silicone. Additionally, thickness 27 and 27' should preferably not add bulk or excessive rigidity or flexibility to the retractor 10. In certain embodiments, the retractor wings 20 and 20' may be temporarily shortened vertically (dimension 30) to place onto the patient's lips and may expand vertically (dimension 30) once released, to aid lip retraction. If the wings 20 and 20' are too rigid or flexible, potentially a result of inappropriate wing thickness 27 and 27', the retraction may be too sensitive to the size of the retractor 10 and a larger variety of retractors may need to be produced.

Figure 3:
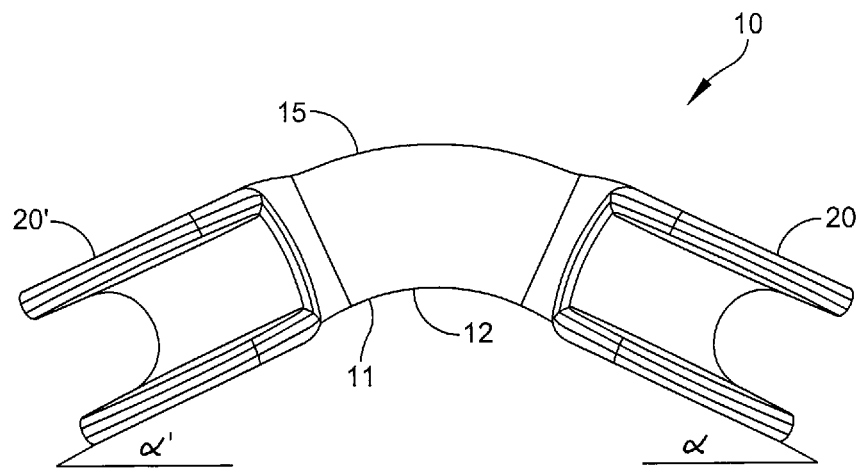
FIG. 3 shows a side view of the lip retractor and guard, in accordance with various embodiments.

FIG. 3 shows a view of the retractor 10 from the superior end, showing the curve 11 of the connector 15 and how the wings 20 and 20' extend at plane angles a and a' from the connector 15. The wing connector 15 is therefore a curved connector as shown in this view, with the curve apex 12 preferentially placed adjacent the inferior lip during use. The elongate wings 20 and 20' extend posteriorly from the curved wing connector 15 and remain approximately on the plane equal to angles $\alpha$ and $\alpha'$. The retractor may be formed as such so as to match or follow the natural contour of the patient's open mouth.

Figure 4:
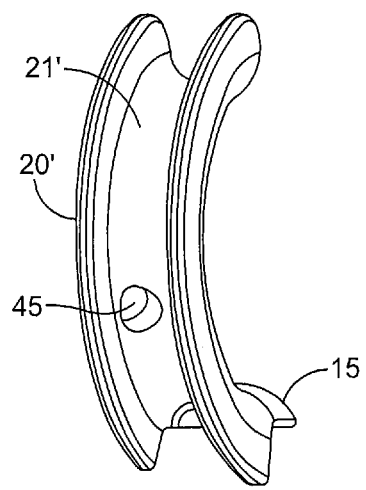
FIG. 4 shows a perspective view of one side of the lip retractor and guard with a suction aperture shown, in accordance with various embodiments.

FIG. 4 shows one wing 20' and part of the wing connector 15, with an aperture 45 in the wing cross section 22'. The aperture 45 is operable to receive a tube end (shown FIG. 7) and the aperture 45 and tube end are cooperatively sized so as to be a frictional fit with each other and keep the tube end in position. Tube end may be in communication with a suction tube and vacuum source, so as to provide a conduit for the removal of electrosurgical by-products and surgical by-products from the oral cavity without requiring a second suction instrument and surgical staff to potentially hold this in place within the cavity. A single occurrence of aperture 45 is shown here; however it is contemplated in alternative embodiments that more than one aperture may be present, or alternatively that aperture 45 may be located on both wings 20 and 20'. In this embodiment, aperture 45 may be preferentially about 0.25 inches in diameter. Aperture 45 is shown placed in an inferior portion of wing 20' so that the connected tubing may efficiently extend or drop away from the retractor 10 and surgical field with minimal suction tubing length back to the vacuum source (not shown here). Aperture 45 is also shown on the wing curved portion 21' and more specifically disposed on the posterior portion of the curve to that the aperture 45 is angled so as to aim suction posteriorly into the patient's mouth for optimum suction.

Figure 6:
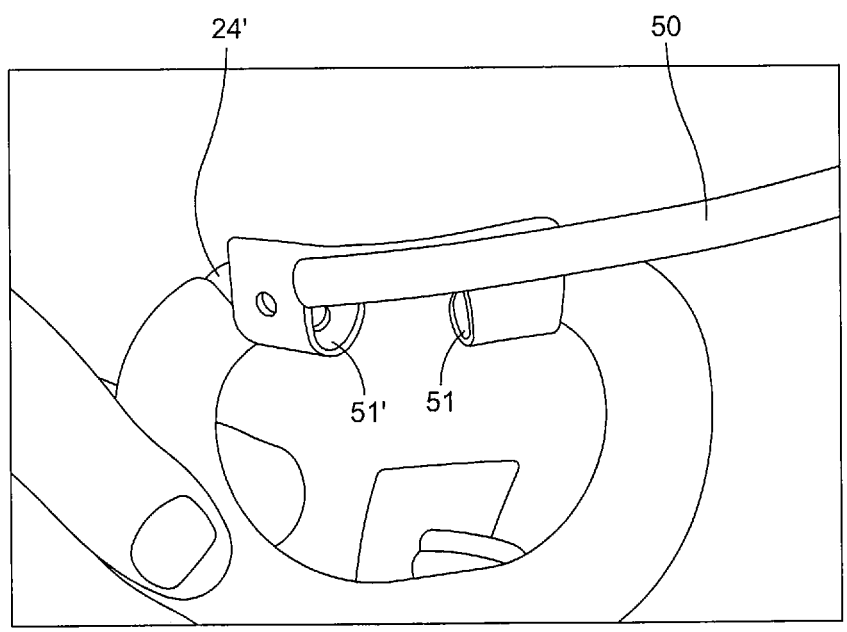
FIG. 6 shows a tooth retractor accommodated between lip retractor free ends, in accordance with various embodiments.

FIG. 5 shows the retractor 10 with the wing connector 15 and gap, 16 so as to allow instrumentation to fit between the retractor 10 and lips (not shown here). More specifically the instrumentation may slide between the inferior portion of wing connector 15 and superior portion of inferior lips (not shown here). A tongue retractor 55 is shown in FIG. 5 as an example of instrumentation. FIG. 6 shows the retractor 10 with a tooth retractor 50 disposed between the wing free ends 24 and 24'. Tooth retractor 50 may have two end portions 51 and 51' that are operable to cooperatively fit between wing free ends 24 and 24' and not interfere with the free ends 24 and 24'.

Figure 7:
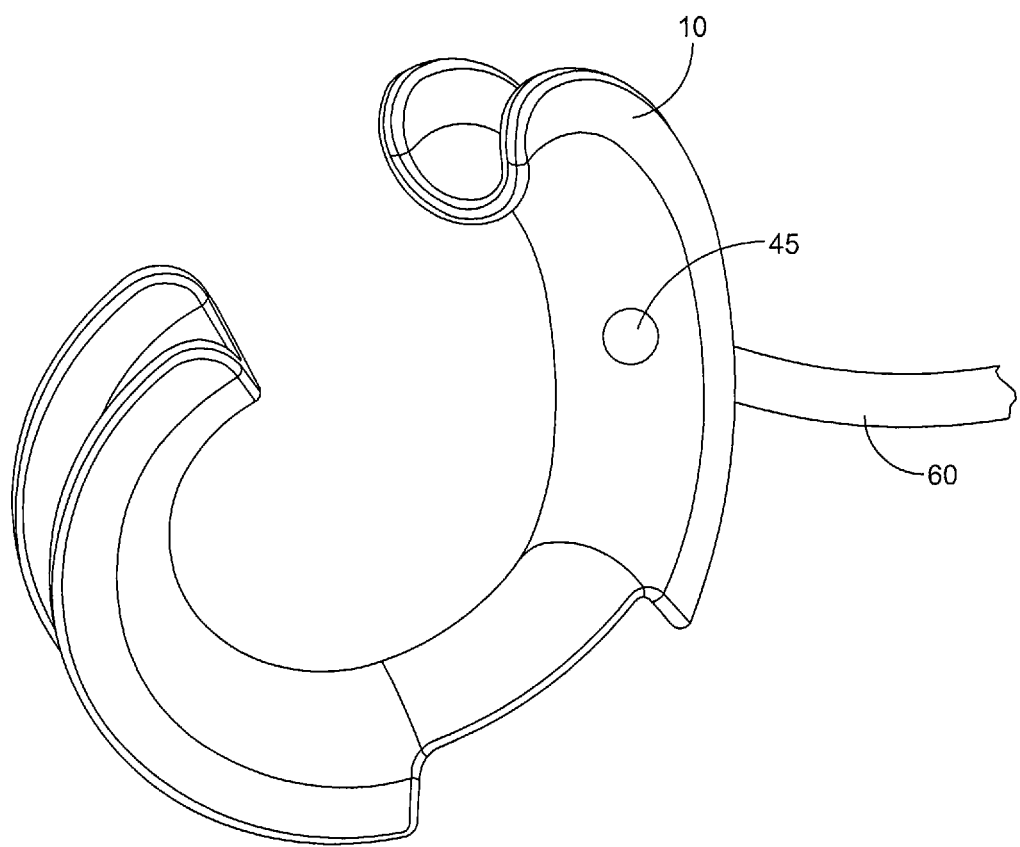
FIG. 7 shows a suction tube assembles with a lip retractor suction aperture, in accordance with various embodiments.
Figure 8:
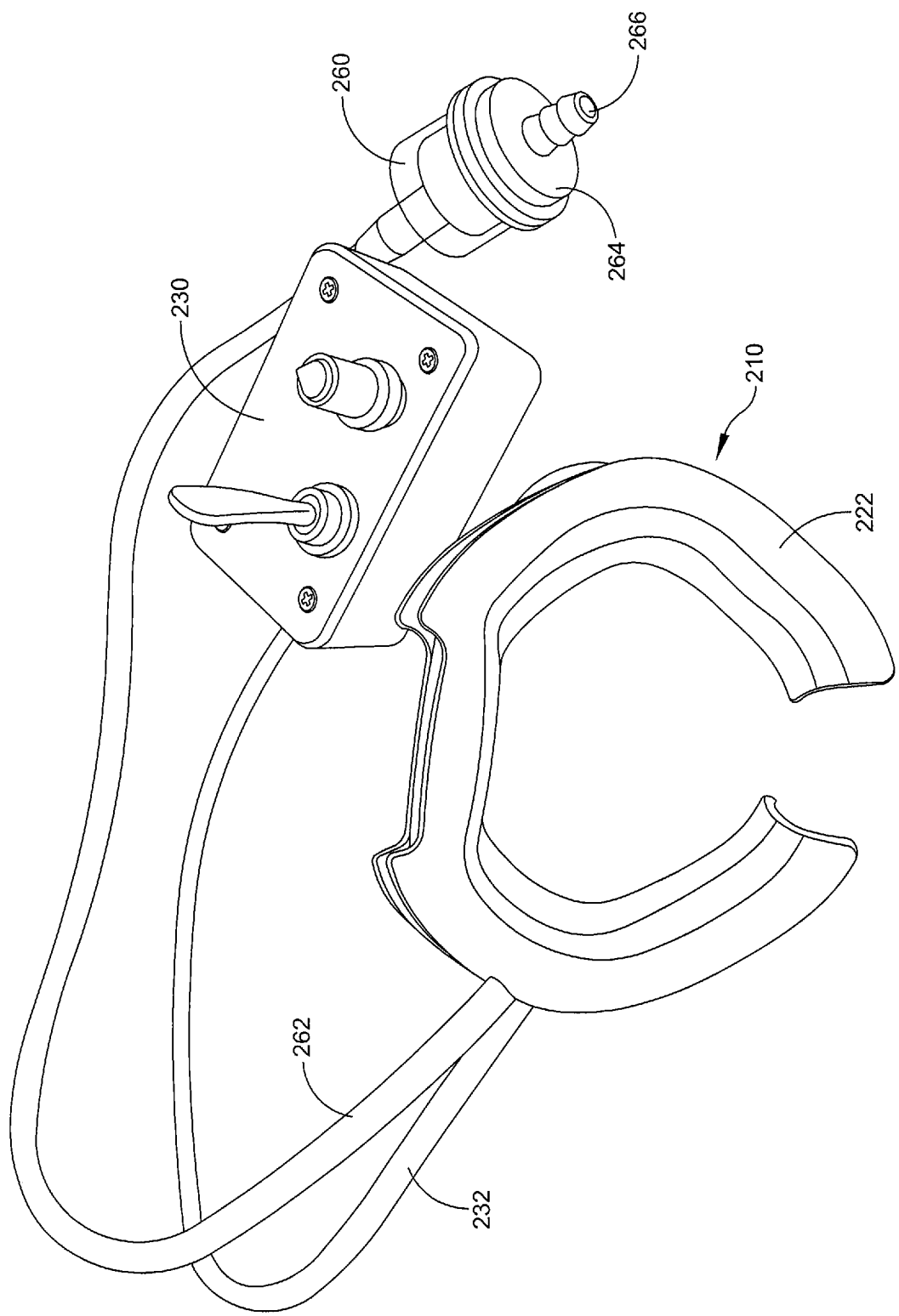
FIG. 8 shows a perspective view of an oral surgical system including a combination lip retractor and guard, a power source, and a suction system, in accordance with various embodiments.
Figure 9:
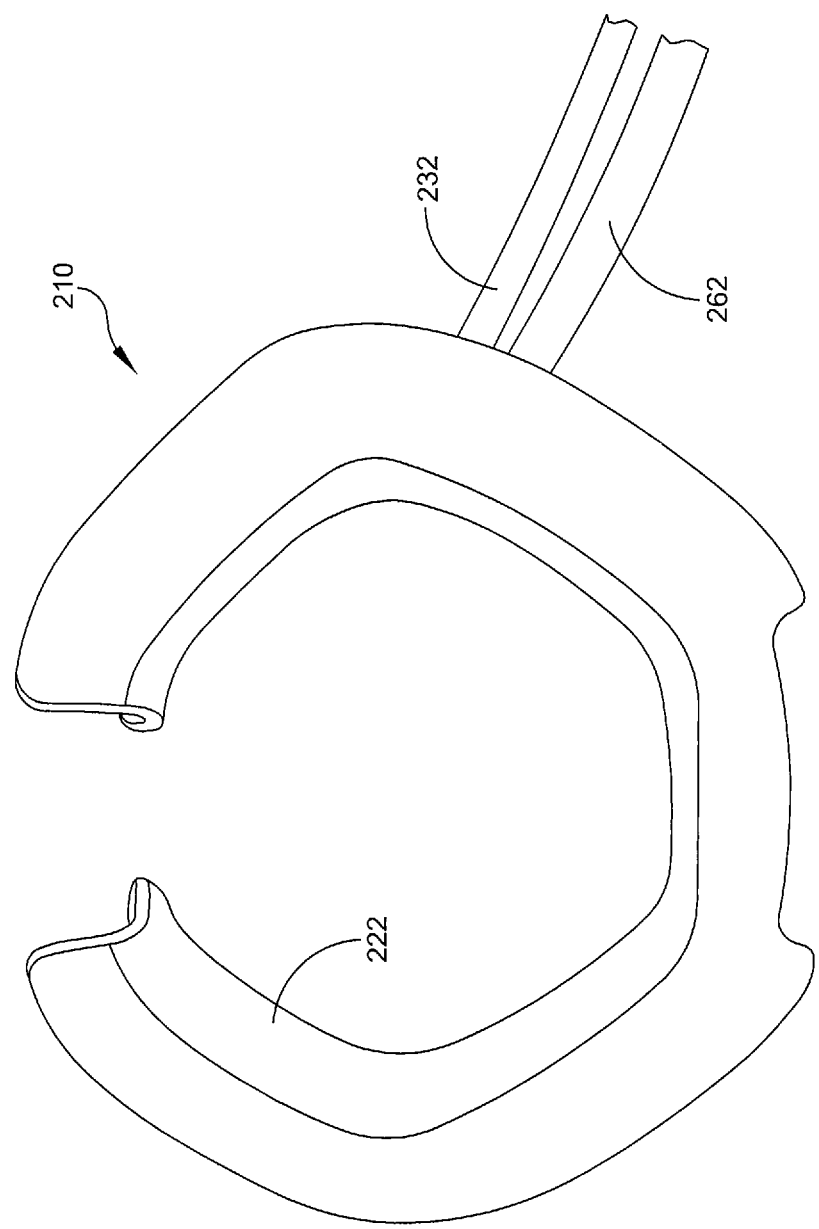
FIG. 9 shows a perspective view of an outer side of the combination lip retractor and guard of FIG. 8, in accordance with various embodiments.
Figure 10:
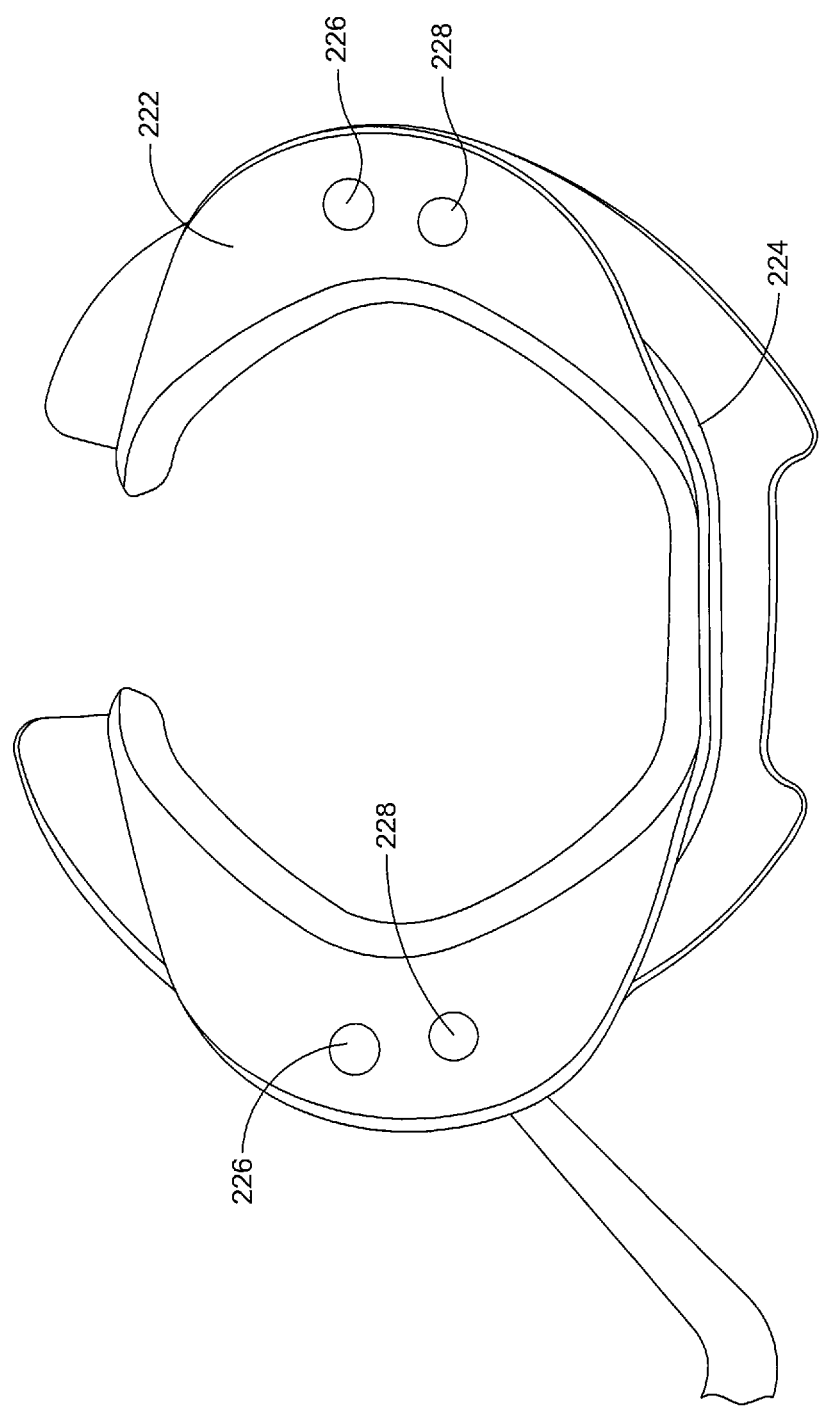
FIG. 10 shows a perspective view of an underside of the combination lip retractor and guard of FIG. 8, in accordance with various embodiments.
Figure 11:
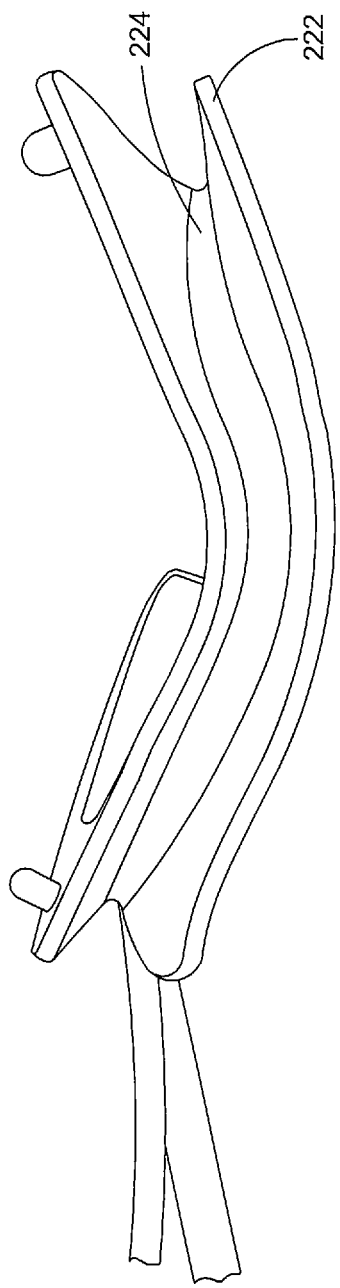
FIG. 11 shows a perspective view of a top of the combination lip retractor and guard of FIG. 8 and an inner liner, in accordance with various embodiments.
Figure 12:
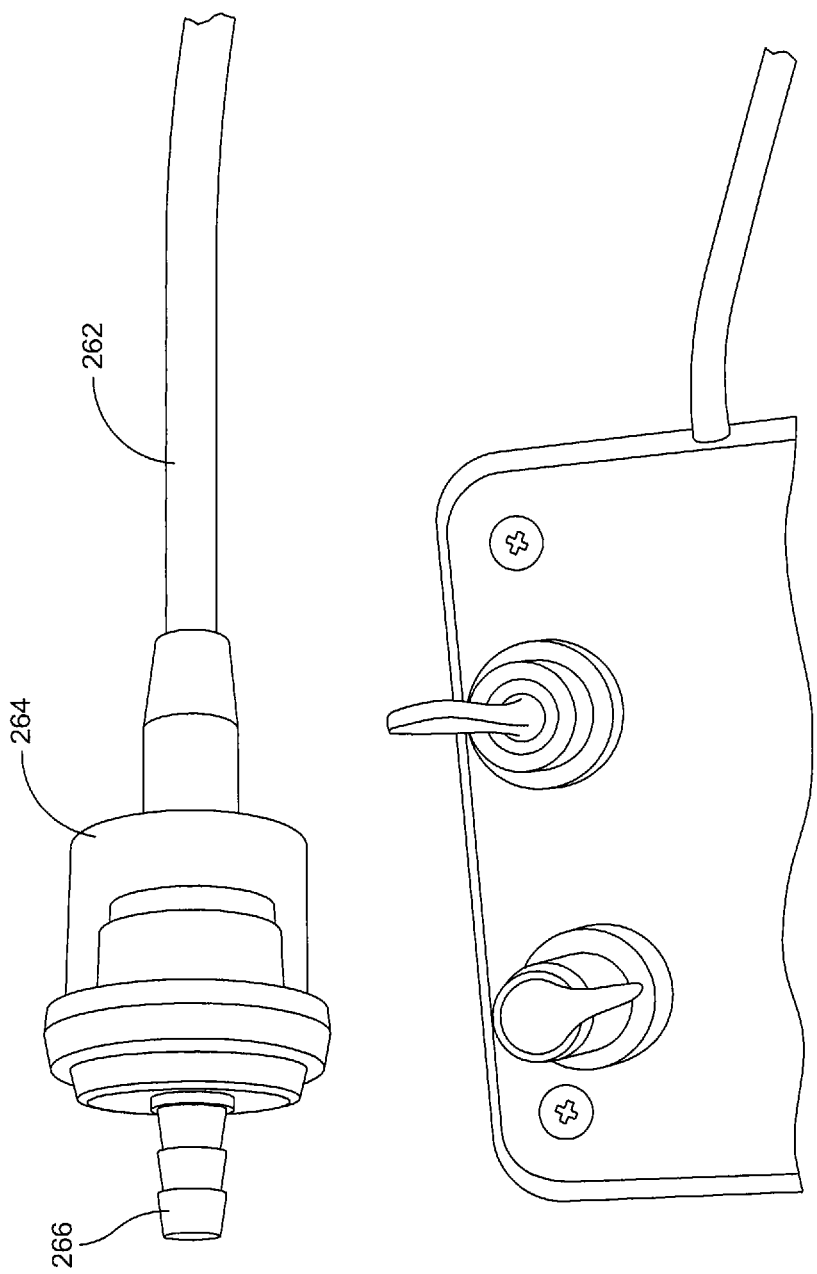
FIG. 12 shows a perspective view of an integrated surgical plume filter attached to suction tubing, in accordance with various embodiments.

FIG. 7 shows the retractor 10 with a suction tube 60 assembled with aperture 45. Shown here, suction tube end is flush with aperture 45. In alternative embodiments the suction tube end may extend through aperture 45 and further posteriorly into patient's mouth for more targeted suction.

FIGS. 8-18 illustrate one embodiment of an oral surgical system 200 including a combination lip retractor and guard 210, a power source 230, and a suction system 260 according to the present disclosure. The combination lip retractor and guard 210 is configured to use in oropharyngeal surgery, although it will be appreciated by those skilled in the art that the combination lip retractor and guard 210 may be used in any suitable oral procedure or surgery. The combination lip retractor and guard 210 is similar to the combination lip retractor and guard 10 described in conjunction with FIGS. 1-7, and similar description is not repeated herein. The combination lip retractor and guard 210 comprises an outer shell 222 and an inner liner 224 (see FIG. 11). An outer side (see FIG. 9) is sized and configured to fit over the lips and oral opening of a patient. An inner side (see FIG. 10) is sized and configured to allow easy access into an oral cavity of a patient. The inner liner 224 is sized and configured to fit within and couple to the outer shell 222. The combination lip retractor and guard 210 is sized and configured to be received within an oral opening of a patient.

Figure 13:
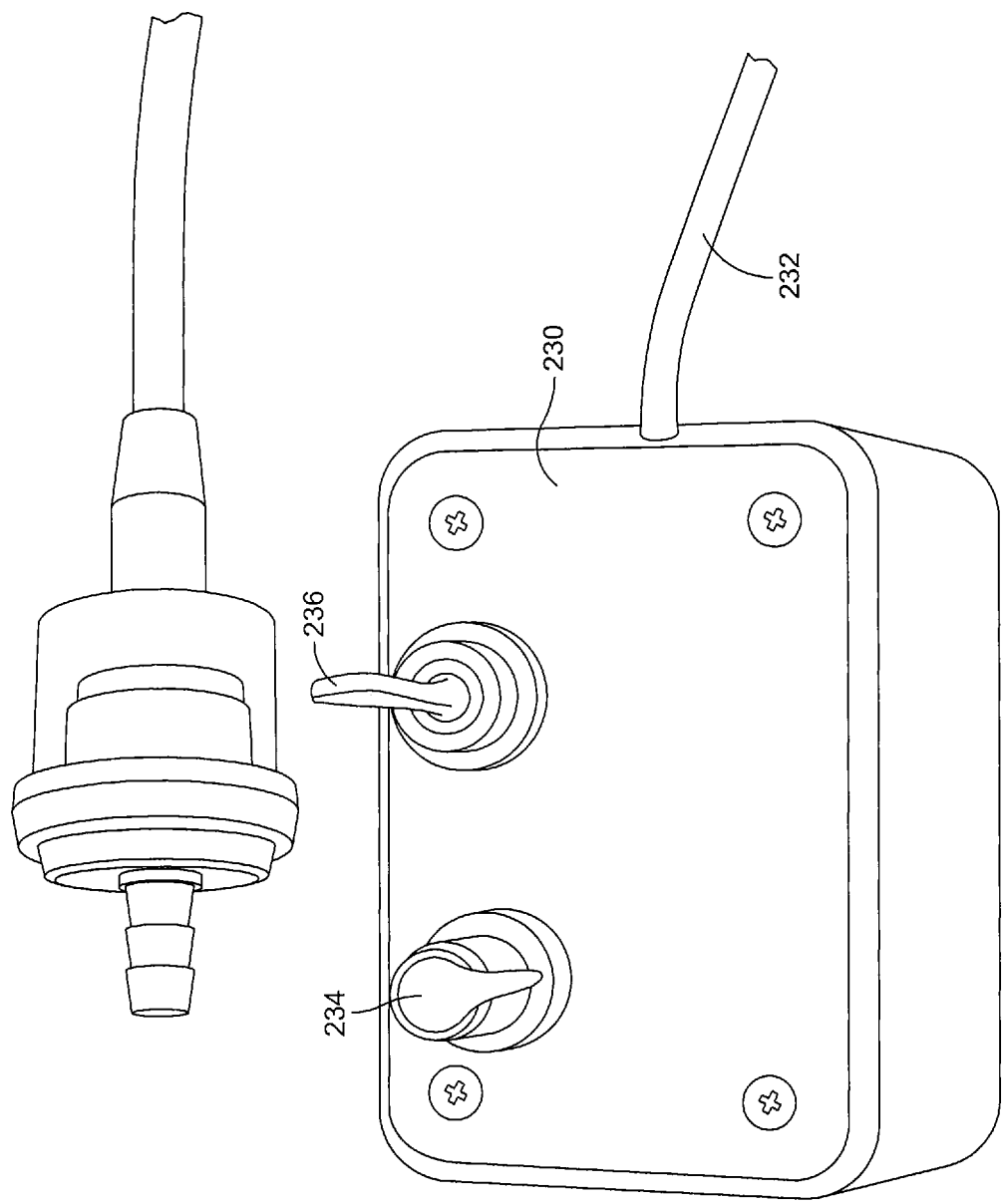
FIG. 13 shows a perspective view of an integrated light-emitting diode (LED) power source apparatus, in accordance with various embodiments.
Figure 14:
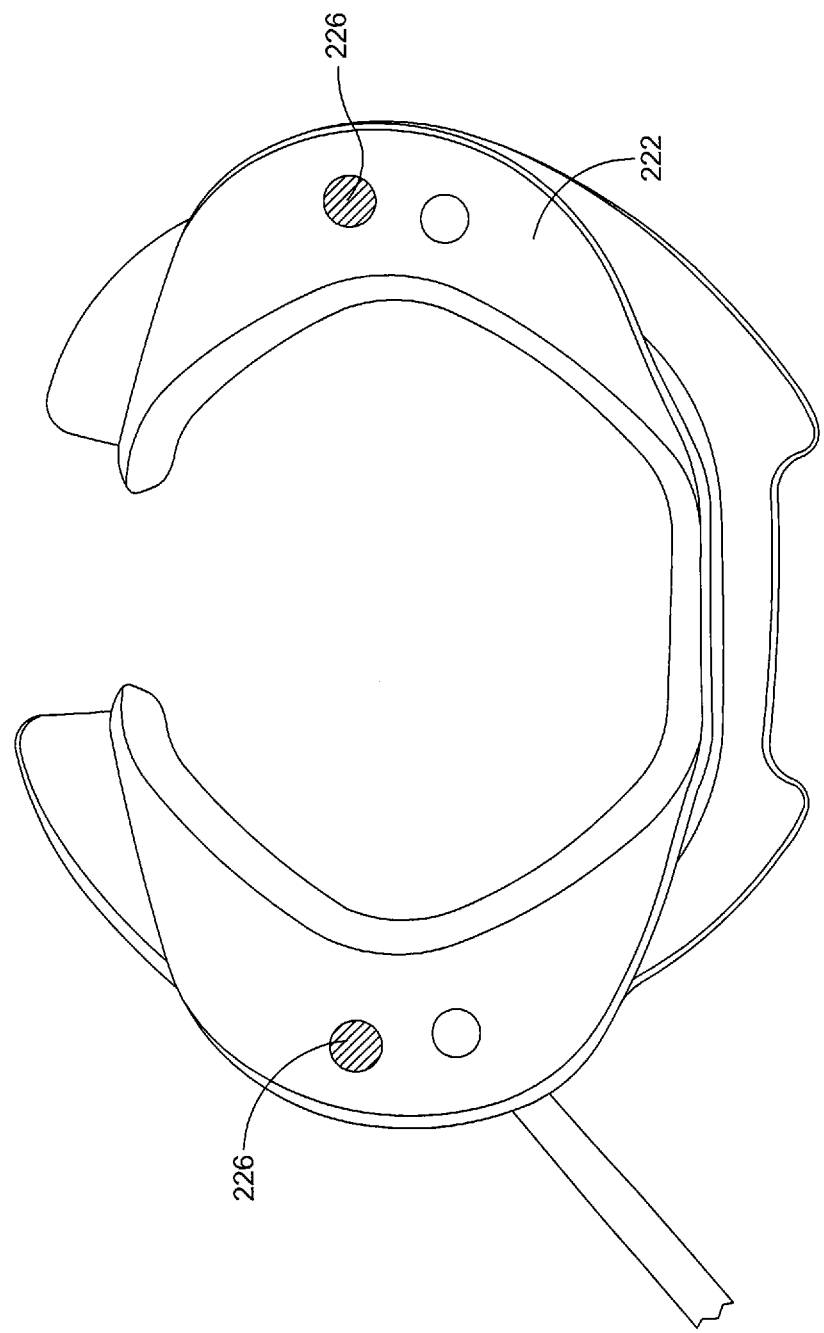
FIG. 14 shows a perspective view of the underside of the lip retractor having integrated white light emitting diodes in an activated position, in accordance with various embodiments.
Figure 15:
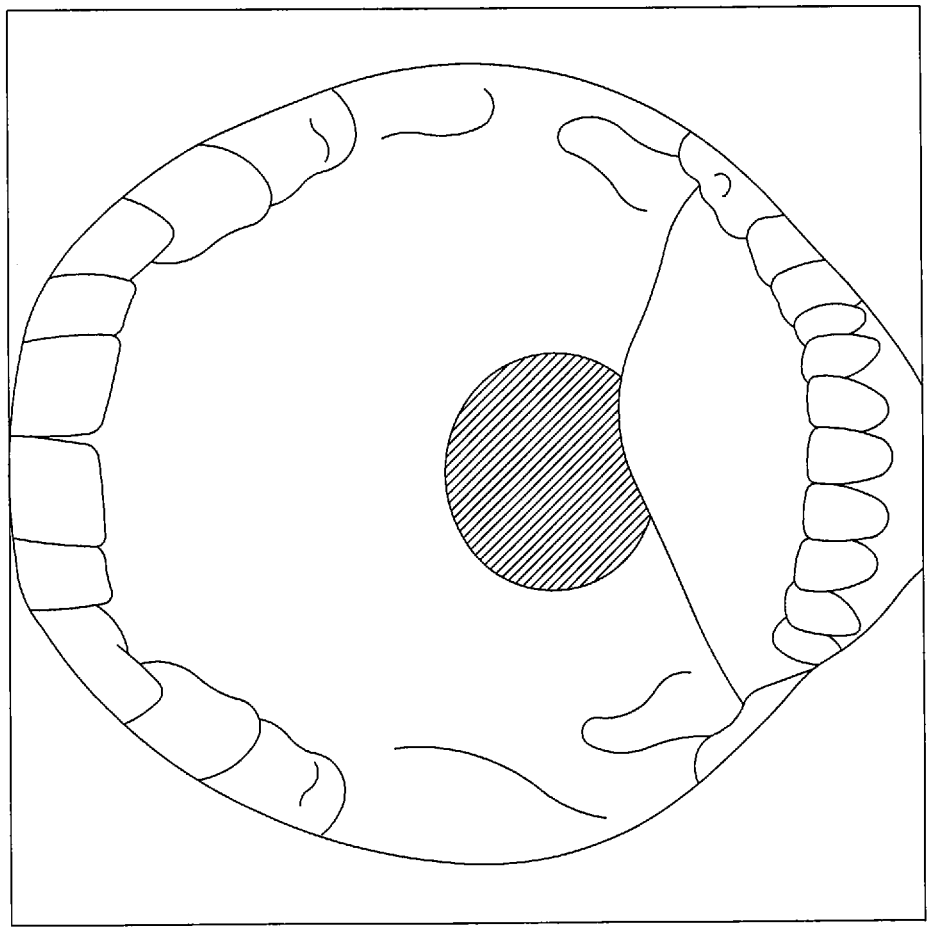
FIG. 15 shows a patient oral cavity illuminated by integrated white light emitting diodes of the combination lip retractor and guard of FIG. 8, in accordance with various embodiments.
Figure 16:
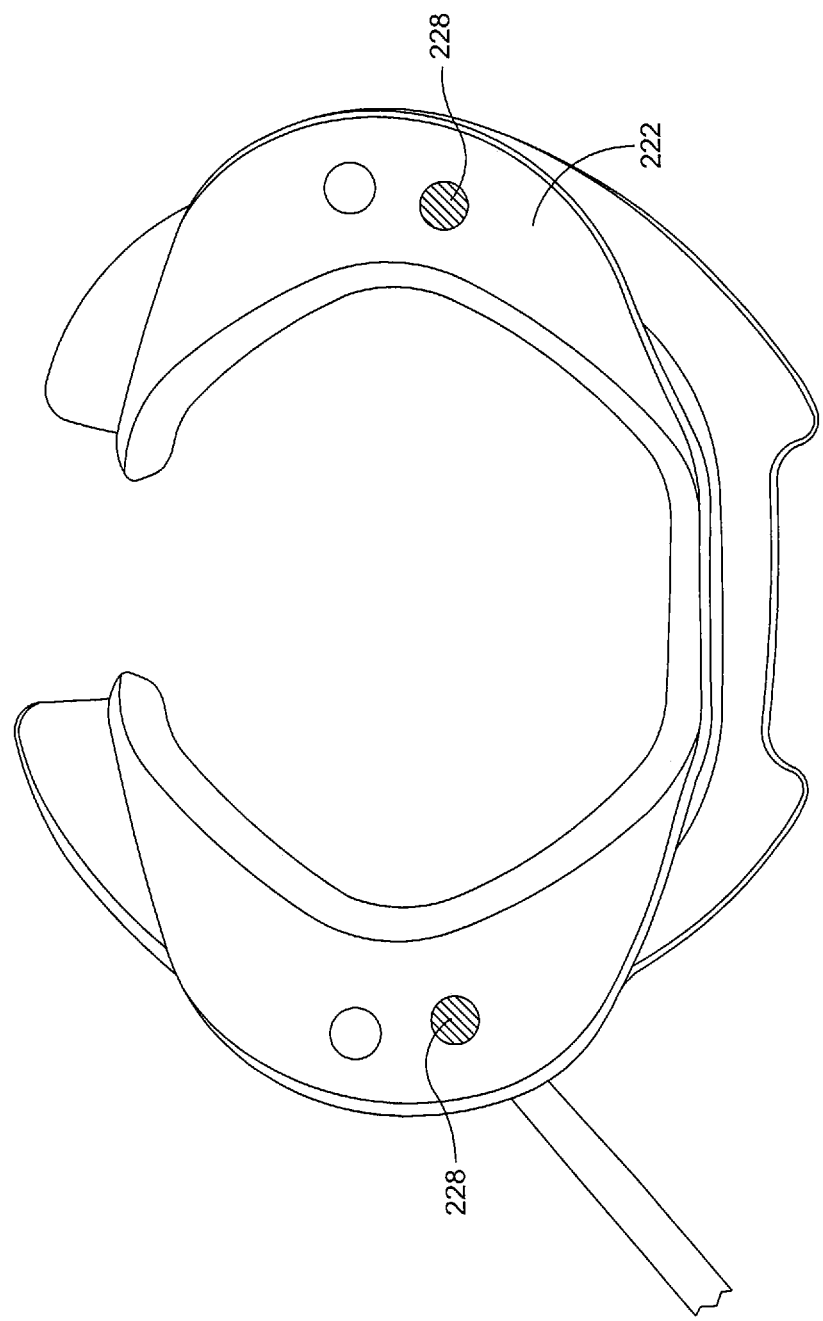
FIG. 16 shows a perspective view of integrated amber light emitting diodes in an activated position, in accordance with various embodiments.
Figure 17:
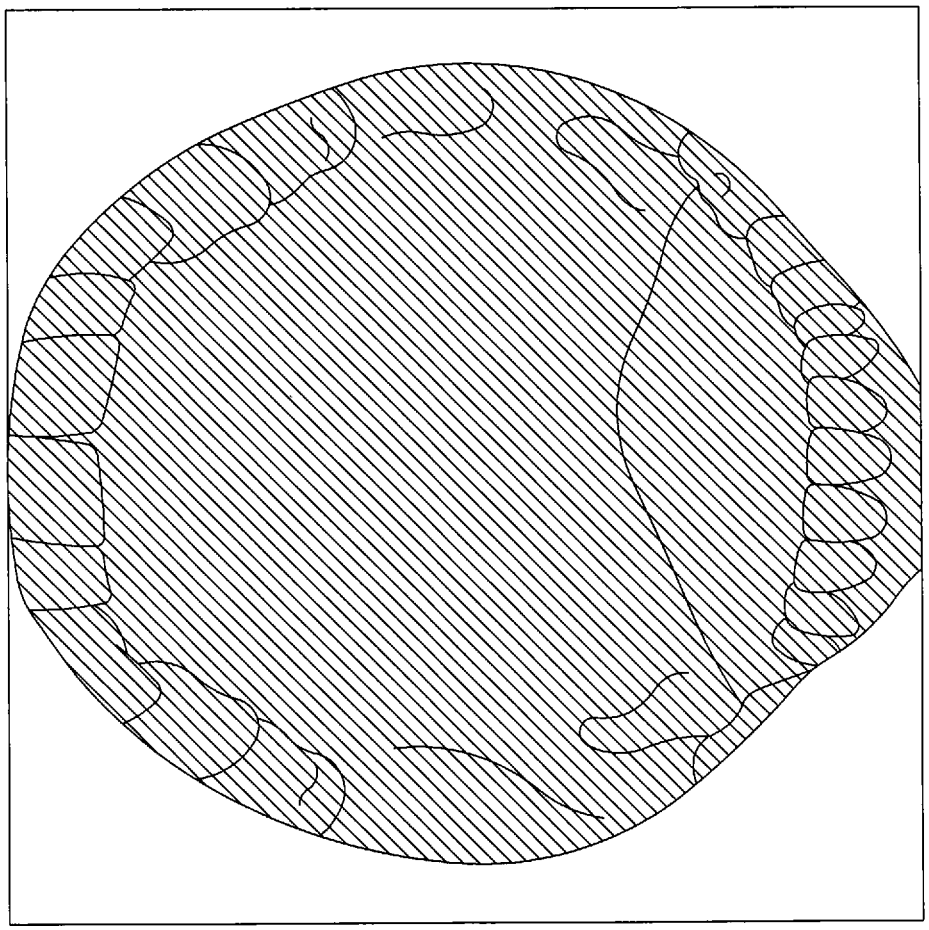
FIG. 17 shows a patient oral cavity illuminated by the integrated amber light emitting diodes of the combination lip retractor and guard of FIG. 8, in accordance with various embodiments.

In some embodiments, the combination lip retractor and guard 210 includes one or more sets of integrated light-emitting diodes (LEDs) 226, 228 (see FIG. 13). The integrated LEDs 226, 228 are configured to provide one or more wavelengths of light to an oral cavity (or other body cavity) during surgery. For example, in some embodiments, the integrated LEDs 226, 228 are positioned on an underside (or internally-facing side) of the combination lip retractor and guard 210. Positioning integrated LEDs, 226, 228 on the inside of the combination lip retractor and guard 210 prevents the LEDs 226, 228 from interfering with the operating path while increasing effectiveness through proximity to patient anatomy. In some embodiments, a first set of integrated LEDs 226 are configured to provide one or more wavelengths of light to illuminate the internal cavity of the patient during surgery. For example, in one embodiment, the first set of integrated LEDs 226 are configured to provide a white spectrum light (see FIGS. 17 & 18). The white spectrum light illuminates the internal cavity of the patient, allowing a clinician to operate within the internal cavity without the use of other illumination sources, such as, for example, a head lamp.

In some embodiments, the combination lip retractor and guard 210 includes a second set of integrated LEDs 228 configure to provide illumination. The second set of integrated LEDs 228 are configured with one or more combinations of light wavelength, output, distance, and viewing angle to maximize visualization of blood vessels during surgery. For example, in the illustrated embodiment, the second set of integrated LEDs 228 are configured to provide a wavelength of light at a predetermined distance and viewing angle that assists in identifying blood vessels located at or near the surface of the surgical site. In various embodiments, the second set of integrated LEDs 228 may be configured to provide amber spectrum light (about 570 nm to about 633 nm), blue spectrum light (about 380 nm to about 500 nm), combinations of wavelengths, such as, for example, a combination of red spectrum light (about 633 nm to about 660 nm) and green spectrum light (about 555 nm to about 570 nm), and/or any other suitable single or combination of spectrums. The wavelength of the second set of integrated LEDs 228 provides contrast between a feature of interest (such as, for example, blood vessels) and surrounding tissue. For example, in the illustrated embodiment, the second set of integrated LEDs 228 include amber spectrum LEDs. When the second set of integrated LEDs 228 illuminates the internal cavity, the amber spectrum light causes blood vessels to appear black and contrast with surrounding tissue (see FIG. 17). In other embodiments, the second set of integrated LEDs 228 include blue spectrum LEDs that cause the blood vessels to appear neon. By highlighting the blood vessels 250 (see FIG. 20), the second set of LEDs allow the surgeon to easily identify and treat vessels 250 before the vessels 250 bleed, such as may be caused during inspection of tonsillar fossa after tonsil removal and before extubation. Although referred to herein as first and second sets of LEDs 226, 228, it will be appreciated that the various embodiments of the combination lip retractor and guard may include only one of the first set of LEDs 226 or the second set of LEDs 228.

In some embodiments, the one or more sets of integrated LEDs 226, 228 are coupled to an LED power supply 230. The LED power supply 230 is coupled to the one or more sets of integrated LEDs 226, 228 through a power cord 232 coupled to and/or formed integrally with the combination lip retractor and guard 210. The LED power supply 230 is configured to provide a drive voltage to the one or more sets of integrated LEDs 226, 228. In some embodiments, the LED power supply 230 includes one or more power switches, such as, for example, a three-position switch 234. The three-position switch 234 is configured as an on-off-on switch and allows one of the first set of LEDs 234 or the second set of LEDs 228 to be activated. In other embodiments, each of the sets of LEDs 226, 228 may be coupled to a separate power switch formed integrally with the LED power supply 230.

In some embodiments, the LED power supply 230 includes an intensity control 236. The intensity control 236 is configured to control the intensity of one or more of the sets of integrated LEDs 226, 228. For example, in the illustrated embodiment, the intensity control 236 includes a potentiometer. Rotation of the potentiometer changes the resistance of the power circuit, increasing or decreasing the intensity of the light produced by the first set of LEDs 226 or the second set of LEDs 228. The intensity control 236 may comprise any suitable circuit element, such as, for example, a potentiometer, an autotransformer dimmer, a solid-state dimmer, and/or any other suitable dimmer. In some embodiments, the LED power supply 230 includes an battery (not shown). In some embodiments, the LED power supply 230 comprises a cord (not shown) configured to couple the LED power supply 230 to an external electrical source, such as, for example, a wall socket. The LED power supply 230 may be configured to charge an internal battery while coupled to an external electrical source.

In some embodiments, the combination lip retractor and guard 210 includes an integrated suction system 260. The integrated suction system 260 is configured to provide suction to an internal cavity during a surgical procedure. For example, in some embodiments, the combination lip retractor and guard 210 is configured for use in oral surgeries, such as, for example, tonsillectomy. The integrated suction system 230 is configured to evacuate fumes and other gases from the oral cavity/throat generated during surgery.

In some embodiments, the integrated suction system 260 includes a suction hose 262 coupled to the combination lip retractor and guard 210. The suction hose 262 extends into a suction hole defined by the combination lip retractor and guard 210. The suction hole (see FIGS. 19A-19C) position the suction hose 262 at an effective range to capture contaminants generated during surgery. The suction hose 262 extends proximally from the combination lip retractor and guard 210 to a surgical plume 264. The surgical plume 264 includes a filter configured to filter exhaust gas and fumes evacuated from the internal body cavity. In some embodiments, the surgical plume 264 includes a high particulate filtration efficiency (PFE) material. The surgical plume 264 may be releasably coupled to the suction hose 264 to provide for replacement of the surgical plume 264. In other embodiments, the surgical plume 264 is permanently coupled to the suction hoses 262. The surgical plume 264 includes a suction port 266 sized and configured to couple to a suction device to generate suction through the suction hose 262.

Figure 18:
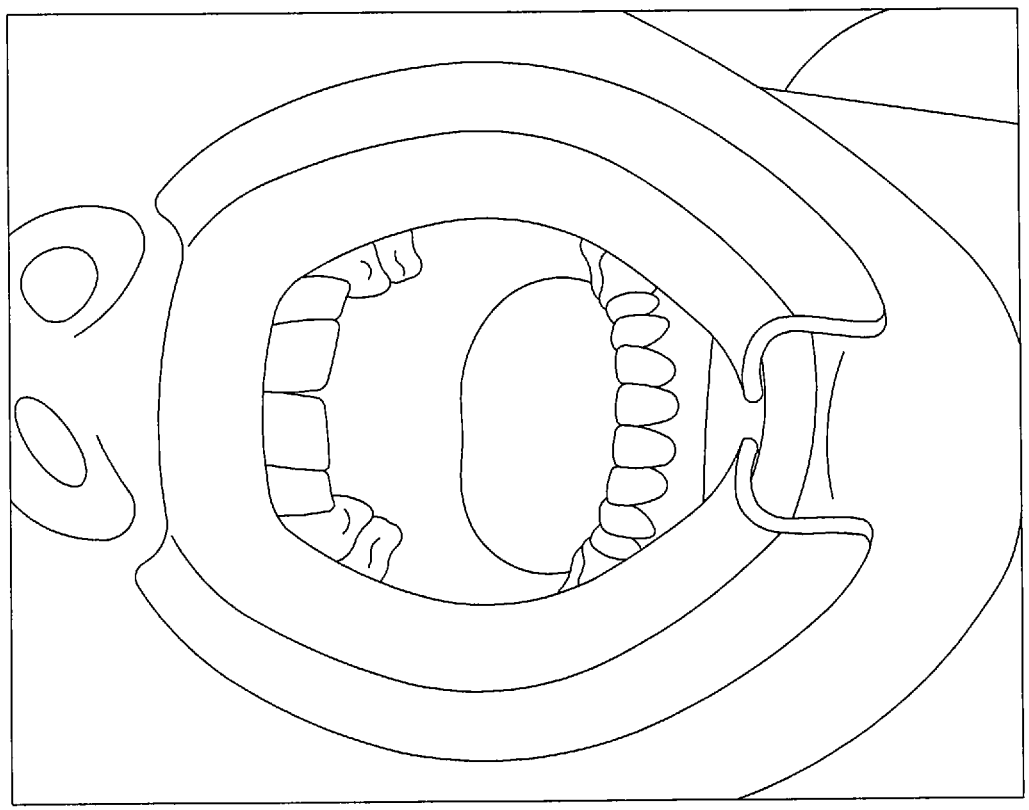
FIG. 18 shows the combination lip retractor and guard of FIG. 8 in position in a patient's oral cavity, in accordance with various embodiments.

FIG. 18 illustrates one embodiment of the combination lip retractor and guard 210 coupled to an oral cavity of a patient. As shown in FIG. 18, the combination lip retractor and guard 210 extends about and covers the majority of the lips and oral opening of a patient. The combination lip retractor and guard 210 is sized and configured to prevent accidental contact between surgical instruments and the oral opening. In some embodiments, the combination lip retractor and guard 210 comprises a semi-flexible, heat resistant, non-flammable material configured to prevent transfer of energy, such as heat and/or electrical energy, between a surgical instrument and the oral opening/lips of a patient. For example, in some embodiments, the combination lip retractor and guard 210 is formed of flexible polyurethane and/or silicon. In other embodiments, other suitable insulating materials may be used.

In some embodiments, the combination lip retractor and guard 210 is configured to be used with a surgical mouth gag (not shown). For example, in some embodiments, the combination lip retractor and guard 210 is configured to be used with a surgical moth gag to immobilize the tongue and/or to extend the jaws. Example surgical mouth gags include, but are not limited to, Crowe-Davis, Mcgivor, Whitehead, Molt, Denhart, Roser-Koenig, Fergusson-Ackland, Jennings, Kilner-Doughty, Davis-Boyle, Dingmann, and/or FK-WO TORS surgical mouth gags.

Figure 19A:
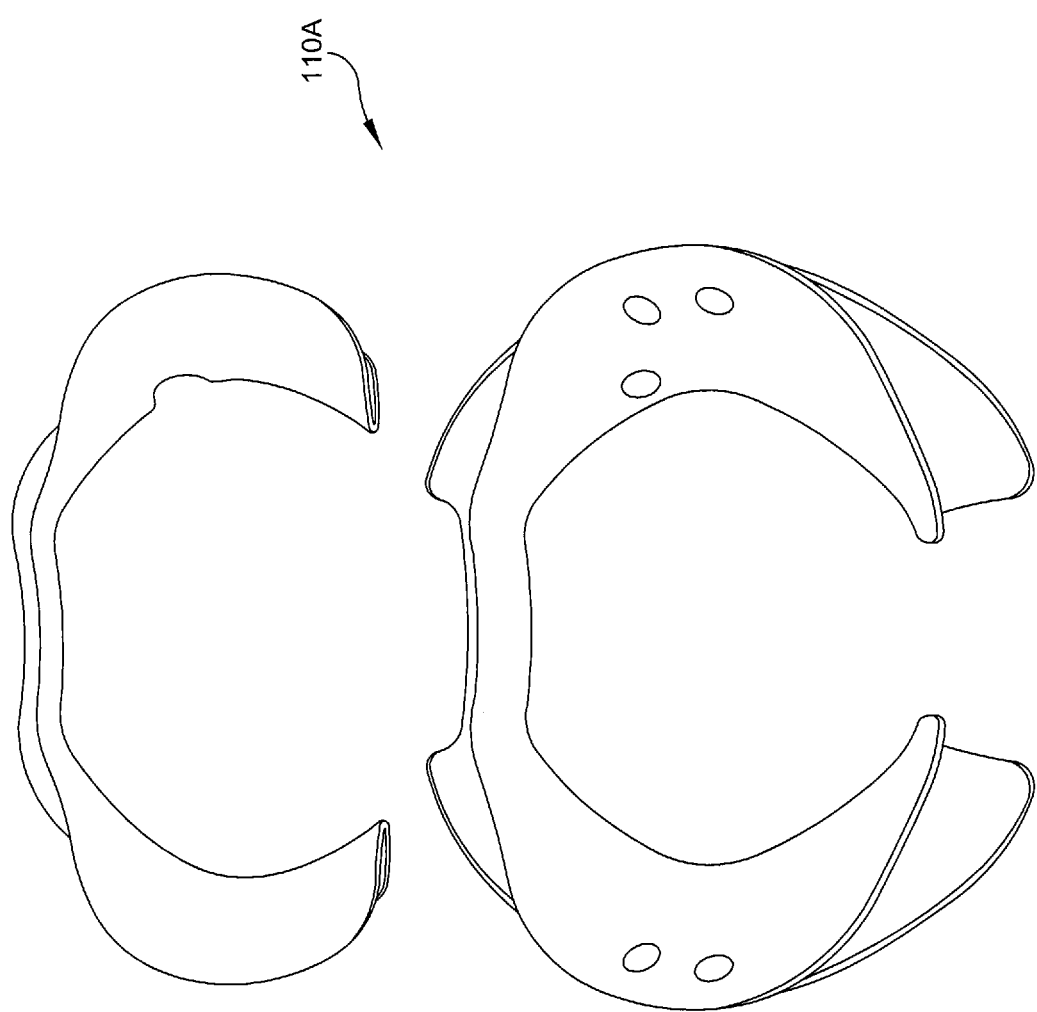
FIGS. 19A-19C show various stereolithography (SLA) parts of an inner liner and an outer shell of a lip retractor in various states of assembly, in accordance with various embodiments.
Figure 19B:
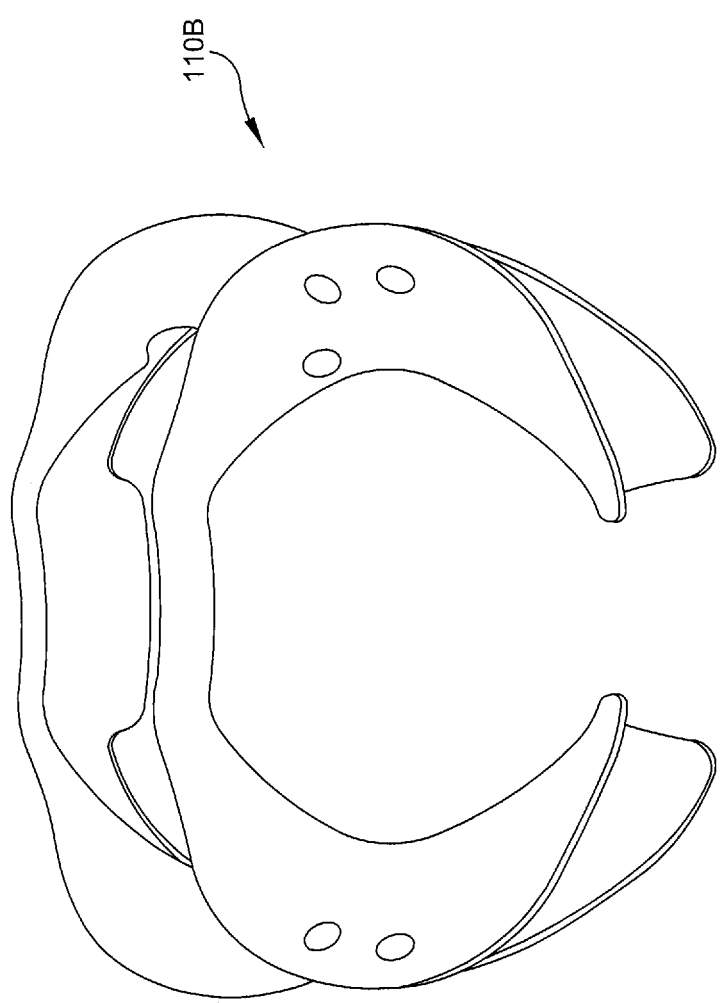
Figure 19C:
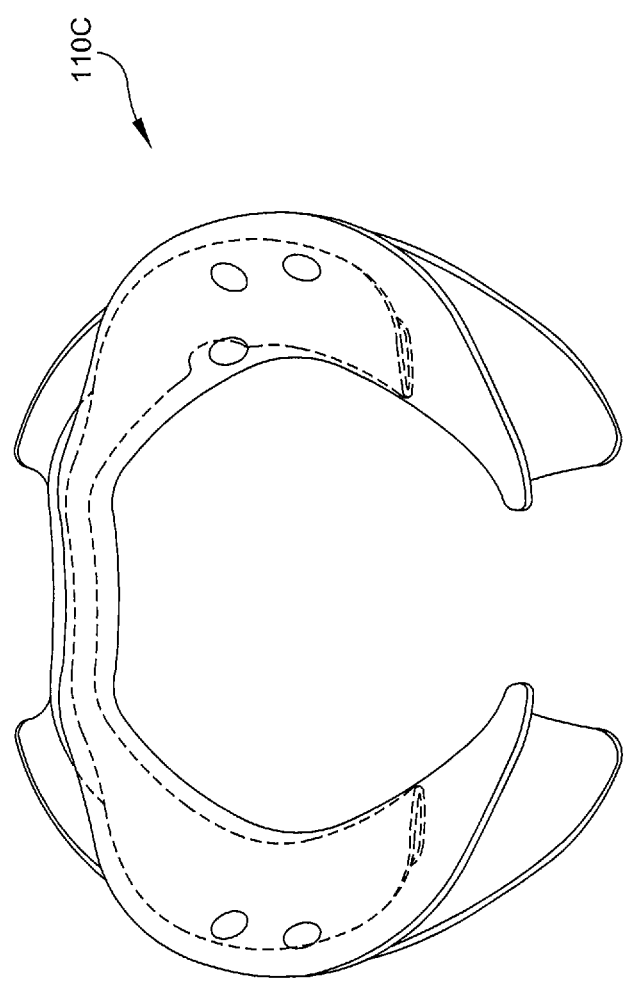

FIGS. 19A-19C show stereolithography (SLA) parts of one embodiment of a combination lip retractor and guard 110 in various states of assembly. FIG. 19A illustrates an outer shell 122 and an inner liner 124 in a separated position. FIG. 19B illustrates the outer shell 122 and the inner liner 124 in a partially assembled position. FIG. 19C illustrates the outer shell 122 and the inner liner 124 in a fully assembled position. The inner liner 124 is releasably coupled to the outer shell 122 in the fully assembled position.

FIGS. 20A-20I shows one embodiment of a combination lip retractor and guard 310a. The combination lip retractor and guard 310a can have varying sizes, including, for example, a first or "small size" (A=1.989", B=1.614", C=2.810", D=0.755", E=1.396", F=0.656", G=3.443", H=1.287", I=0.630"), a second or "intermediate size" (A=2.29", B=1.848", C=3.063", D=0.755", E=1.409", F=0.777", G=3.743", H=1.349", I=0.630"), and/or a third or "large size" (A=2.604", B=1.210", C=3.440", D=0.755", E=1.423", F=0.951", G=4.058", H=1.499", I=0.630"). The various measurements and sizes discussed herein are exemplary, and it will be understood that the combination lip retractor and guard 310a may be manufactured in any suitable size and having any suitable dimensions and/or ratios.

Figure 21:
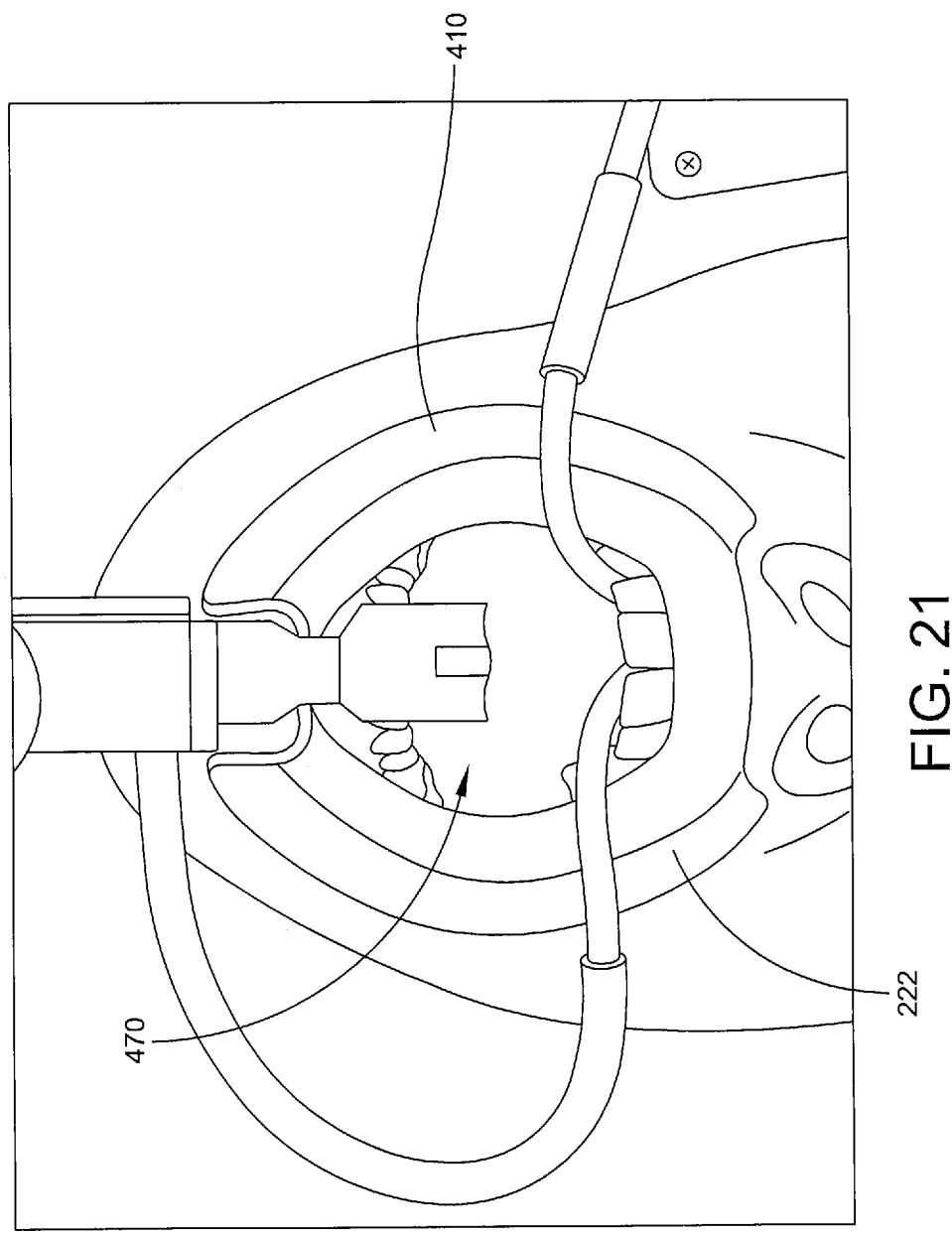
FIG. 21 shows a combination lip retractor and guard positioned in the oral cavity of a surgical patient under oral mouth gag suspension, in accordance with various embodiments.

FIG. 21 illustrates a combination lip retractor and guard 410 positioned in an oral cavity of a surgical patient under oral mouth gag suspension, in accordance with some embodiments. The lip retractor and guard 410 includes at least one LED (not shown) configured to illuminate an oral cavity 470 of a patient. The at least one LED may be any suitable color, such as, for example, a white LED, a red LED, and/or any other color LED. In some embodiments, the lip retractor and guard 410 includes a cutout 472 configured to accommodate one or more additional surgical tools.

Figure 22:
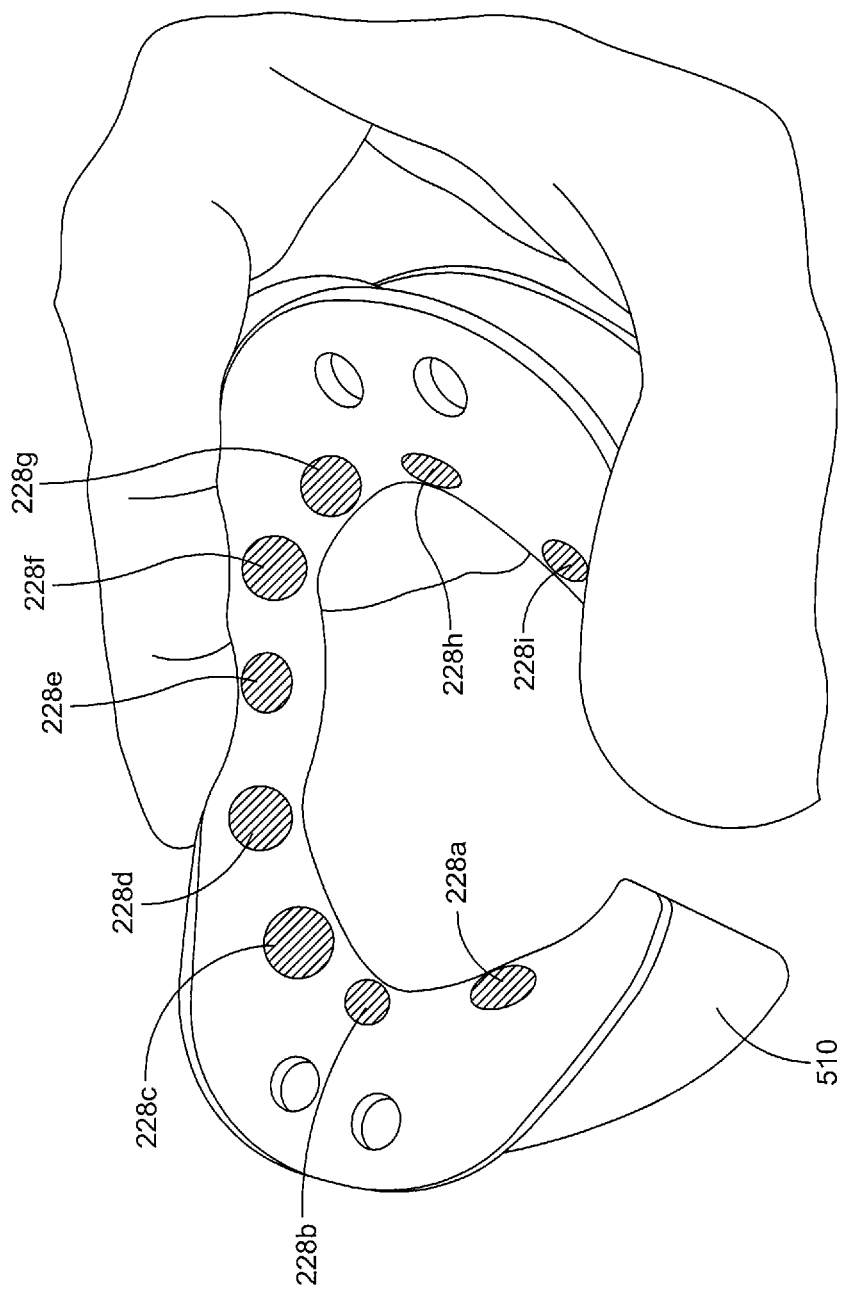
FIG. 22 shows a combination lip retractor and guard having a plurality of LEDs to provide increased illumination from a plurality of angles within the oral cavity, in accordance with various embodiments.
Figure 23:
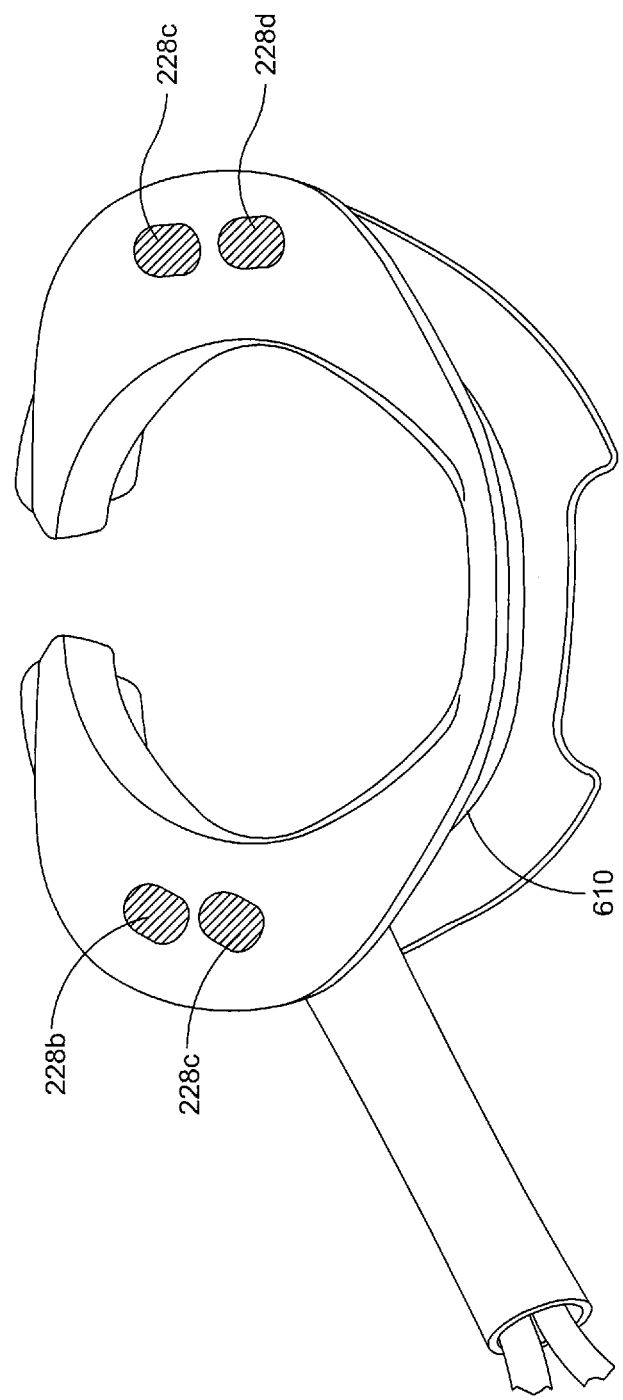
FIG. 23 illustrates a combination lip retractor and guard having a plurality of LEDS for increased illumination from a plurality of angles, in accordance with various embodiments.

FIGS. 22 and 23 illustrate lip retractor and guards 510, 610 having a plurality of LEDs therein, in accordance with various embodiments. As shown in FIG. 22, in some embodiments, a lip retractor and guard 510 can include a plurality of LEDs 228a-228i distributed about the lip retractor and guard 510. For example, in some embodiment, the lip retractor and guard 510 includes seven LEDs, although it will be appreciated that any suitable number of LEDs can be distributed about the lip retractor and guard 510. The LEDs can constitute any suitable LEDs such as, for example, one or more white LEDs, one or more red LEDs, and/or any other suitable combination of LEDS. As shown in FIG. 23, in some embodiments, a lip retractor and guard 610 can include a plurality of LEDs 228a-228d located only on a first side and a second side of a lip retractor and guard 610.

Although various embodiments of the combination lip retractor and guard are illustrates herein for use in oral surgery, it will be appreciated that the combination lip retractor and guard and/or various elements of the disclosed embodiments may be configured for use in any suitable surgery. For example, in some embodiments, a guard may be configured for use in additional body openings, such as, for example, a vaginal cavity opening, an anal cavity opening, an open surgery opening, a wound opening, and/or any other suitable body opening.

What is claimed is:

1. A surgical guard comprising:
   a first arcuate wing comprising a first end and a second end;
   a second arcuate wing comprising a first end and a second end; and
   a wing connector extending between the first end of the first arcuate wing and the first end of the second arcuate wing, wherein the first arcuate wing, the second arcuate wing, and the wing connector are sized and configured to couple to an oral cavity, wherein the first arcuate wing and the second arcuate wing extend posteriorly from the wing connector such that the first arcuate wing, second arcuate wing, and wing connector are each configured to contact a portion of a surgical patient's lip when coupled to the oral cavity, wherein the first arcuate wing, the second arcuate wing, and the wing connector define a continuous troughed cross-section comprising a curved base and laterally extending walls, wherein the laterally extending walls are sized and configured to insulate the lips and oral commissure of the surgical patient.

2. The surgical guard of claim 1, comprising a first plurality of light-emitting diodes (LEDs) formed integrally with an inner side of each of the first wing and the second wing, wherein the first plurality of LEDs provide a wavelength of light configured to illuminate a body cavity during a surgical procedure.

3. The surgical guard of claim 2, comprising a second plurality of LEDs formed integrally with the inner side of each of the first wing and the second wing, wherein the second plurality of LEDs provide a wavelength of light configured to highlight blood vessels located at or near a surface of the body cavity.

4. The surgical guard of claim 3, wherein the wavelength of light provided by the second plurality of LEDs comprises at least one of an amber wavelength or a blue wavelength.

5. The surgical guard of claim 1, wherein at least one of the first wing or the second wing defines at least one suction aperture therein, and wherein the surgical guard is configured to provide suction to a body cavity through a suction tube inserted through the suction aperture.

6. The surgical guard of claim 5, comprising a filter coupled to a proximal end of the suction tube.

7. The surgical guard of claim 1, wherein the at least one suction aperture is defined on a posterior side of the at least one of the first arcuate wing or the second arcuate wing.

8. The surgical guard of claim 1, wherein the first arcuate wing, the second arcuate wing, and the wing connector comprises at least one of a polyurethane material or a silicone material.

9. The surgical guard of claim 1, wherein the second end of the first arcuate wing and the second end of the second arcuate wing are spaced apart to allow surgical instrumentation access to the oral cavity.

10. The surgical guard of claim 1, wherein the wing connector comprises a curved connector, and wherein the first arcuate wing extends from the curved connector in a first plane and the second arcuate wing extends from the curved connector in a second plane.

11. A method of retracting and guarding the oral commissure, comprising:
   reducing a horizontal dimension of a lip retractor and guard such that the lip retractor and guard fit within an oral cavity proximal to oral commissures, wherein the lip retractor and guard comprises a first arcuate wing comprising a first end and a second end, a second arcuate wing comprising a first end and a second end, and a wing connector coupling the first end of the first arcuate wing and the first end of the second arcuate wing;
   nesting a first oral commissure within the first arcuate wing and a second oral commissure within the second arcuate wing; and
   releasing the lip retractor and guard such that the horizontal dimension of the lip retractor and guard increases and retracts the oral cavity away from a predefined surgical field, wherein the first arcuate wing and the second arcuate wing extend posteriorly from the wing connector such that the first arcuate wing, second arcuate wing, and wing connector are each configured contact a portion of a surgical patient's lip when coupled to the oral cavity, wherein the first arcuate wing, the second arcuate wing, and the wing connector define a continuous troughed cross-section comprising a curved base and laterally extending walls, and wherein the laterally extending walls are sized and configured to insulate the lips and oral commissure of the surgical patient.

12. The method of claim 11, comprising performing a surgical operation through an opening defined by the first arcuate wing, the second arcuate wing, and the wing connector.

13. The method of claim 11, comprising aspirating one or more fluids or electroscopy by-products via a suction tube disposed at least partially through an aperture formed in at least one of the first arcuate wing or the second arcuate wing.

14. The method of claim 11, comprising positioning a surgical instrument between the second end of the first arcuate wing and the second end of the second arcuate wing.

15. A lip retractor and guard, comprising:
a first arcuate shaped wing and a second arcuate shaped wing, wherein each of the first arcuate shaped wing and the second arcuate shaped wing include a first end and a second end;
a wing connector extending between the first end of the first arcuate shaped wing and the first end of the second arcuate shaped wing, wherein at least one of the first arcuate shaped wing, the second arcuate shaped wing, or the wing connector are deformable to compress the first arcuate shaped wing and the second arcuate shaped wing, wherein the first arcuate wing and the second arcuate wing extend posteriorly from the wing connector such that the first arcuate wing, second arcuate wing, and wing connector are each configured to contact a portion of a surgical patient's lip when coupled to an oral cavity, wherein the first arcuate wing, the second arcuate wing, and the wing connector define a continuous troughed cross-section comprising a curved base and laterally extending walls, and wherein the laterally extending walls are sized and configured to insulate the lips and oral commissure of the surgical patient; and
wherein at least one light-emitting diode (LED) is formed integrally with an inner side of at least one of the first arcuate shaped wing, the second arcuate shaped wing, and the wing connector, and wherein the at least one LED is configured to illuminate a body cavity.

16. The lip retractor and guard of claim 15, wherein at least one of the first arcuate shaped wing, the second arcuate shaped wing, and the wing connector define an aperture therein, wherein the aperture defines a pathway for a suction tube from outside the body cavity to the body cavity.

17. The lip retractor and guard of claim 15, wherein the second end of the first arcuate shaped wing and the second end of the second arcuate shaped wing comprise spaced apart free ends defining an opening to allow surgical instrumentation access to an oral cavity.

18. The lip retractor and guard of claim 15, comprising:
a first plurality of LEDs having a first wavelength; and
a second plurality of LEDs having a second wavelength.

19. The lip retractor and guard of claim 18, wherein at least one of the first wavelength or the second wavelength is configured to highlight blood vessels located at or near the surface of the body cavity.

* * * * *